United States Patent [19]
Wilk

[11] Patent Number: 5,544,651
[45] Date of Patent: Aug. 13, 1996

[54] MEDICAL SYSTEM AND ASSOCIATED METHOD FOR AUTOMATIC TREATMENT

[76] Inventor: Peter J. Wilk, 185 West End Ave., New York, N.Y. 10023

[21] Appl. No.: 198,095

[22] Filed: Feb. 17, 1994

Related U.S. Application Data

[63] Continuation-in-part of Ser. No. 941,569, Sep. 8, 1992, Pat. No. 5,145,167.

[51] Int. Cl.⁶ .................. A61B 5/00; A61M 5/00
[52] U.S. Cl. ............ 128/633; 128/637; 128/660.02; 128/661.04; 128/667; 128/702; 604/890.1; 604/891.1; 604/50; 604/51; 604/52; 604/53; 604/93; 604/174; 604/179; 604/272; 604/280
[58] Field of Search .................. 128/632–634, 128/637, 653.1, 666–667, 696, 702, 660.02, 661.04, 662.06; 604/890.1, 891.1, 20–21, 31, 48–53, 93, 164, 174, 179, 272, 280

[56] References Cited

U.S. PATENT DOCUMENTS

| | | |
|---|---|---|
| 4,206,755 | 6/1980 | Klein .................................. 604/50 |
| 4,315,513 | 2/1982 | Nawash et al. . |
| 4,335,711 | 6/1982 | Olson . |
| 4,344,435 | 8/1982 | Aubin . |
| 4,525,165 | 6/1985 | Fischell . |
| 4,529,401 | 7/1985 | Leslie et al. ................ 128/DIG. 1 |
| 4,567,898 | 2/1986 | Plugge et al. . |
| 4,596,575 | 6/1986 | Rosenberg et al. . |
| 4,687,468 | 8/1987 | Gianturco . |
| 4,805,623 | 2/1989 | Jöbsis .............................. 128/633 |
| 4,822,337 | 4/1989 | Newhouse et al. . |
| 4,911,168 | 3/1990 | Davis . |
| 4,981,139 | 1/1991 | Pfohl . |
| 5,022,402 | 6/1991 | Schieberl et al. . |
| 5,069,662 | 12/1991 | Bodden . |
| 5,190,522 | 3/1993 | Wojcicki et al. .................... 604/31 |
| 5,203,336 | 4/1993 | Iida et al. . |
| 5,305,745 | 4/1994 | Zacouto .......................... 128/637 |

Primary Examiner—Krista M. Zele
Attorney, Agent, or Firm—R. Neil Sudol; Henry D. Coleman

[57] ABSTRACT

A medical device comprises a sensor for at least periodically measuring a predetermined physiological parameter of a patient and for generating a signal encoding a measured value of the physiological parameter. A comparator is operatively connected to the sensor for comparing the measured value of the physiological parameter with a predetermined threshold value for the physiological parameter to determine whether the measured value of the physiological parameter has passed the threshold value. A treatment component is operatively connected to the comparator for automatically injecting a predetermined chemical composition into the patient upon a determination by the comparator that the measured value of the physiological parameter has passed the threshold value. An attachment element is provided for attaching the sensor, the comparator and the treatment component to the patient.

16 Claims, 8 Drawing Sheets

| 86 | 88 | 90 | 92 | 94 | 96 |
|---|---|---|---|---|---|
| TRANSMITTER CODE | PATIENT CODE | PARAMETER IDENTIFIER | PARAMETER VALUE | MEASURE LOCATION | TIME/ DATE |

MEDICAL SYSTEM AND ASSOCIATED METHOD FOR AUTOMATIC TREATMENT

CROSS-REFERENCE TO RELATED APPLICATION

This application is a continuation-in-part of application Ser. No. 07/941,569 filed Sep. 8, 1992, now U.S. Pat. No. 5,145,167.

BACKGROUND OF THE INVENTION

This invention relates to a medical method for at least partially automatic diagnosis and, optionally, treatment. This invention also relates to a device or system for implementing such a method.

Implantable devices exist for periodically injecting insulin into the vascular system of a diabetic patient. An insulin reservoir is implanted subcutaneously and is periodically refilled via a hyperdermic needle inserted through a self-sealing membrane on the reservoir.

A problem with such a solution is that the amount of insulin injected may be inappropriate to the needs of the particular patient. Insulin is injected automatically, without regard to the condition of the patient.

There are other potentially life threatening conditions which are simply and effectively counteracted by the injection of a selected pharmaceutical agent into the blood stream of the patient. For example, in hyperparathyroidism, the victim suffers from the effects of an increased level of calcium ions in the blood. Chemical compositions are known for lowering the level of calcium. Other conditions which may be treated through the simple administration of known pharmaceutical agents include low blood pressure and cardiac arrythmias. In certain people, for example, an arrythmia arises in response to a bee sting. The potentially life threatening condition can be eliminated by the injection of epinephrine.

A problem with all such conditions is the timely administration of medication. For various reasons, a victim may succomb to his or her illness or deficiency or at the very least may experience a lapse in the quality of life. For example, either the onset of a life threatening condition is not recognized or medication is not available immediately.

OBJECTS OF THE INVENTION

An object of the present invention is to provide a device for treating a patient who has a life threatening condition.

Another object of the present invention is to provide to provide such a device for administering medication to a patient.

Another, more particular, object of the present invention is to provide such a device wherein medication is at least generally administered in timely fashion.

A further particular object of the present invention is to provide such a device wherein a life threatening condition is diagnosed and results in the automatic administration of medication.

Yet another object of the present invention is to provide is to provide a related method for treating a patient who has a life threatening condition characterized by possibly recurrent episodes.

Another object of the present invention is to provide to provide such a method for timely administering medication to a patient.

A further particular object of the present invention is to provide such a method wherein a life threatening condition is diagnosed and results in the automatic administration of medication.

These and other objects of the present invention will be apparent from the drawings and detailed descriptions herein.

SUMMARY OF THE INVENTION

A medical device comprises, in accordance with the present invention, a sensor for at least periodically measuring a predetermined physiological parameter of a patient and for generating a signal encoding a measured value of the physiological parameter. A comparator is operatively connected to the sensor for comparing the measured value of the physiological parameter with a predetermined threshold value for the physiological parameter to determine whether the measured value of the physiological parameter has passed the threshold value. A treatment component is operatively connected to the comparator for automatically injecting a predetermined chemical composition into the patient upon a determination by the comparator that the measured value of the physiological parameter has passed the threshold value. An attachment element is provided for attaching the sensor, the comparator and the treatment component to the patient.

According to another feature of the present invention, the sensor includes componentry for detecting a concentration of a blood constitutent such as glucose or calcium ions. For example, the sensor componentry may include a laser diode and a photocell implanted into the patient on opposite sides of a selected blood vessel for detecting glucose level in the blood. In that case, the treatment component includes a catheter or other means for injecting insulin into the patient's vascular system. The laser diode is tuned, upon the attainment of temperature equilibrium inside the patient, to emit electromagnetic radiation of a characteristic frequency absorbed by glucose molecules.

According to further feature of the present invention, the sensor, the comparator and the treatment component are all disposed inside a casing which is attached to a skin surface of the patient via the attachment element. For example, where blood pressure or cardiac rhythm are being monitored, the attachment element may take the form of a wrist band. If necessary, the sensor may be separate from the casing and connected to the comparator and the treatment component via a wire or a receiver/transmitter combination.

Where the treatment component is disposed in a casing outside the patient, the contact or connection with the vascular system of the patient need occur only upon the detection of a potentially life threatening condition. Thus, medication may be introduced into the patient by deliery directly through the skin under high pressure or indirectly via a hypodermic needle which is automatically inserted subcutaneously.

In many cases, it is preferable to have the sensor, the comparator and the treatment component implanted into the patient. This is not ony convenient for the patient but also serves to protect the patient from infection and to protect the device from accidental removal or destruction.

Where the physiological parameter is blood pressure, the sensor includes a monitor for detecting blood pressure of the patient, while the comparator includes means for comparing, with a pre-established blood pressure threshold, blood pressure measurements made by the monitor. An implantable blood pressure monitor may take the form of a flexible slotted cuff inserted about a blood vessel and including a sensitive strain gauge for measuring changes in size of the blood vessel owing to variations in blood pressure.

Where the physiological parameter is an electrocardiographic rhythm, the sensor may include an acousto-electric transducer for detecting pressure waves in the patient arising from the patient's heart action. The device then further comprises an analyzing circuit operatively connected to the acousto-electric transducer for discriminating between acoustic input due to heart action and acoustic pressure waves arising from other sources. The comparator is operatively connected to the analyzing circuit for comparing an electrocardiographic rhythm, as determined through the sensor and the analyzing circuit, with a plurality of thresholds characterizing normal and abnormal cardiac rhythms.

A medical method comprises, in accordance with the present invention, the steps of (a) at least periodically measuring a predetermined physiological parameter of a patient, (b) generating a signal encoding a measured value of the physiological parameter, (c) automatically comparing the measured value of the physiological parameter with a predetermined threshold value for the physiological parameter to determine whether the measured value of the physiological parameter has passed the threshold value, and (d) automatically injecting a predetermined chemical composition into the patient upon determining that the measured value of the physiological parameter has passed the threshold value.

Pursuant to another feature of the present invention, the measurement or the physiological parameter includes the step of detecting a concentration of a blood constitutent such as glucose In that case, the chemical composition or medication injected into the patient is insulin.

Where the blood constitutent is calcium ions, the chemical composition is preselected to reduce the level of calcium ions in the blood.

Where a photodiode and a photocell are implanted into the patient on generally opposite sides of a blood vessel, the detection of the blood constituent includes the step of operating the photodiode to emit light of a characteristic frequency into the blood vessel. The detection further includes the step of operating the photocell to detect a level of the blood constitutent in the blood of the patient, while the step of injecting includes the step of injecting the chemical composition into a vein or artery of the patient.

Pursuant to a further feature of the present invention, the treatment includes the step of injecting the chemical composition into a blood vessel of the patient through a catheter extending to the blood vessel.

According to an additional feature of the present invention, the steps of measuring, generating, comparing and injecting are all preformed inside the patient by operating devices implanted into the patient.

Alternatively, some of the steps of the method may be performed at least partially outside of the patient. For example, the step of injecting medicaton includes the step of automatically inserting a hypodermic needle subcutaneously. This insertion may be implemented by a solenoid, an electric motor, a hydraulically.

Where the physiological parameter is blood pressure, the step of measuring including the step of detecting blood pressure of the patient. Where the physiological parameter is an electrocardiographic rhythm, the step of measuring may include the step of detecting acoustic pressure waves in the patient to monitor heart action. In the latter case, the method further comprises the step of analyzing detected acoustic pressure waves to discriminate between acoustic pressure waves due to heart action and acoustic pressure waves arising from other sources, while the step of comparing includes the step of comparing an electrocardiographic rhythm, as determined in the steps of deteting and analyzing, with a plurality of thresholds characterizing normal and abnormal cardiac rhythms.

A device and an associated method in accordance with the present invention serve in the treatment of patients who have life threatening conditions and must be treated immediately in order to preserve the individual from possibly debilitating or even fatal consequences.

A device in accordance with the present invention administers medication in timely fashion. without the need for human intervention. Accordingly, mistakes in diagnosis and delays in treatment are obviated.

The device and method of the instant invention are particularly suitable for treating patients who have a life threatening condition which has been generally diagnosed but which is characterized by recurrent episodes. Generally, the patient and those around him must take care to detect recurrences of the condition, in time to administer proper medication.

DETAILED DESCRIPTION

Figure 1:
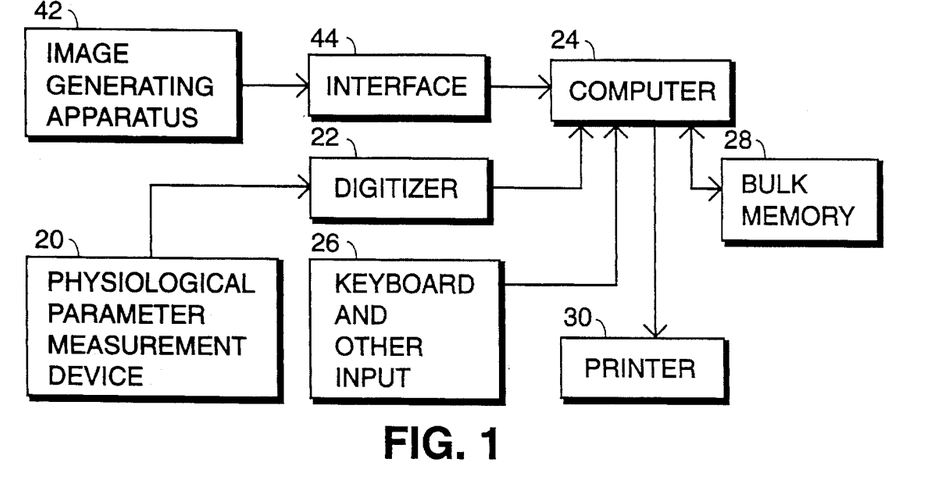
FIG. 1 is a block diagram of a medical diagnostic system.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
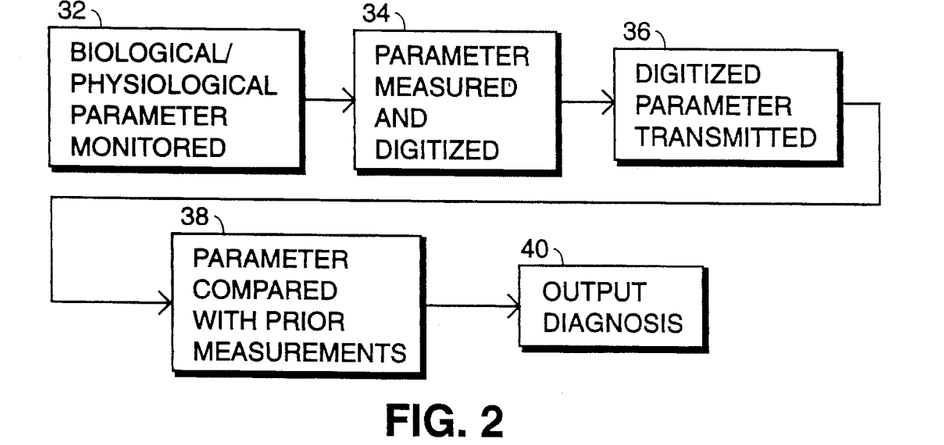
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, the computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, an image generating apparatus or scanner 42 for generating in electrically encoded form a visually readable image of an organic part of the patient. Scanner 42 may take the form of an MRI apparatus, a CAT scanner, an X-ray machine, an ultrasonography apparatus, or a video camera with or without magnification optics for magnifying a sample on a slide. The video camera can be used for obtaining an image of a portion of a patient's skin.

Scanner 42 is connected via an interface 44 to computer 24.

Figure 3:
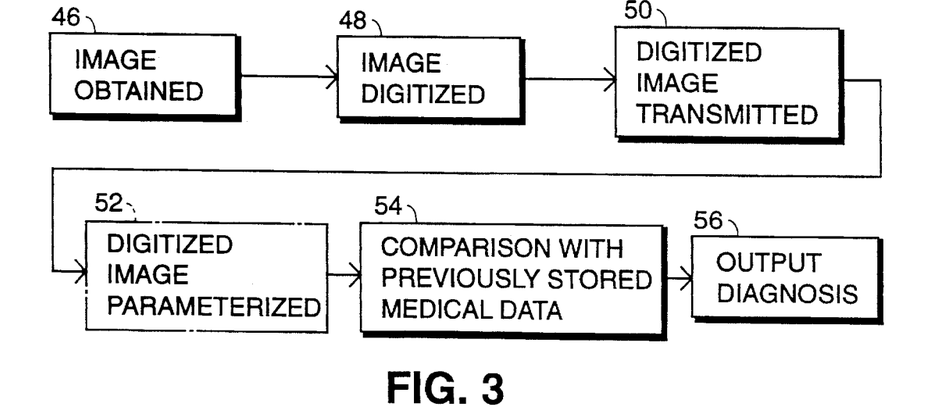
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory 28 may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus or CAT scanner, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 40 (FIG. 3), computer 24 communicates the results of its diagnostic evaluation to a user or patient.

Figure 4:
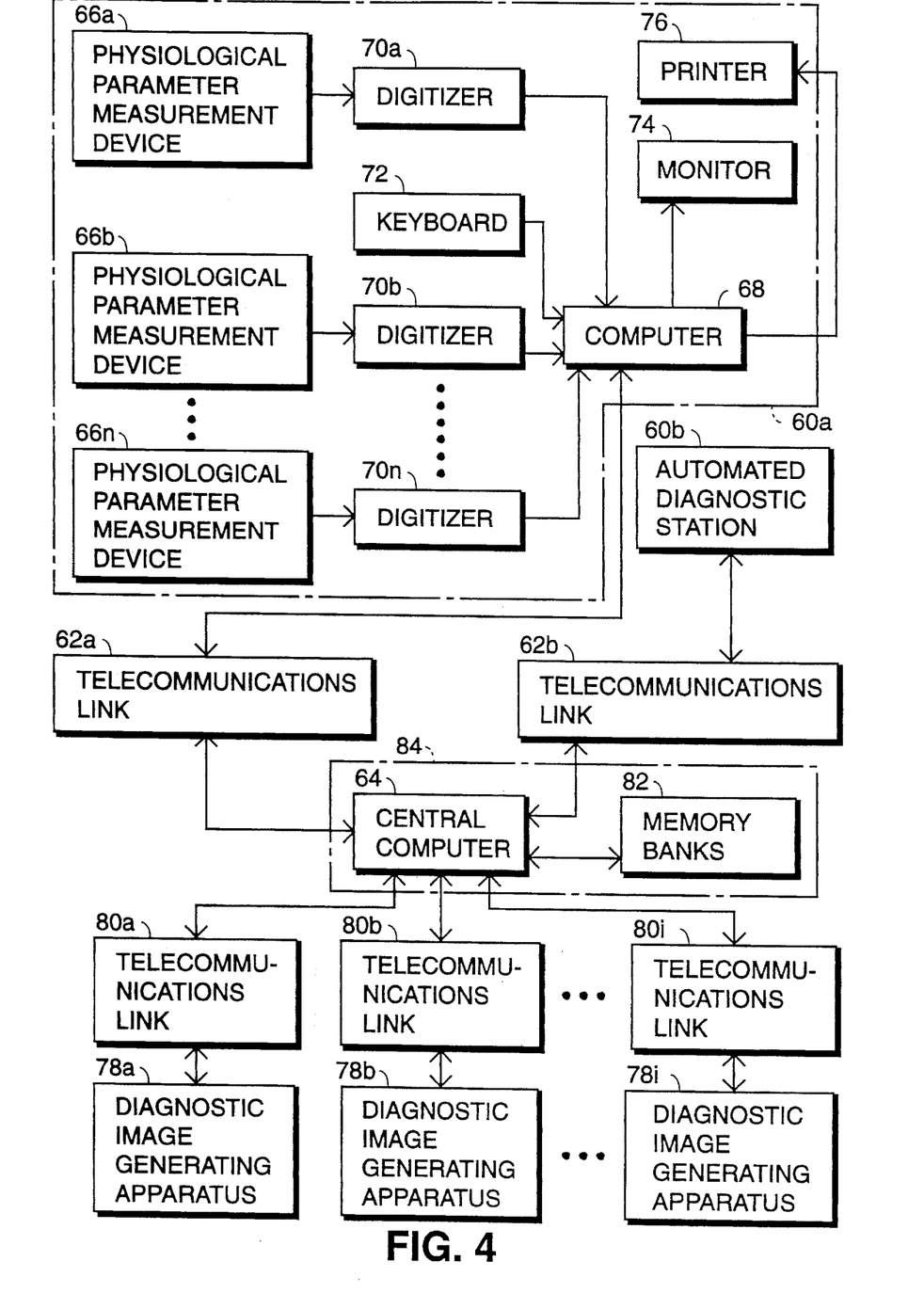
FIG. 4 a block diagram of a further medical diagnostic system.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may resepctively take the form of an electronic thermometer, an electronic blood pressure gauge, a pulmonary function apparatus, a doppler study apparatus, an EEG machine, an EKG machine, an EMG machine, or a pressure measurement device, etc.

Digitizers 70a, 70b, . . . 70n convert normally analog type signals into coded binary pulses and transmit the resulting digital measurement signals to computer 68. Digitizers 70a, 70b, . . . 70n may be incorporated into the housings or casing (not shown) enclosing all or part of the respective monitoring and measuring devices 66a, 66b, . . . 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, . . . 78i are also connected to central computer 64 via respective telecommunications links 80a, 80b, . . . 80i. Scanners 78a, 78b, . . . 78i each generate in electrically encoded form a visually readable image of an organic part of the patient. Scanners 78a, 78b, . . . 78i may each take the form of an MRI apparatus, a CAT scanner, an X-ray machine, an ultrasonography apparatus, or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

Figure 5:
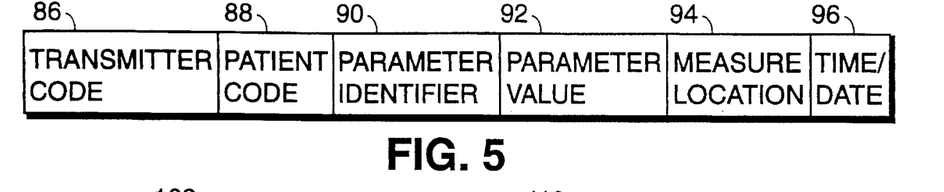
FIG. 5 is a diagram showing the composition of a data string or module used in the system of FIG. 4.

As illustrated in FIG. 5, local computers 24 and 68 transmit information to central computer 64 in data packets or modules each include a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

Figure 6:
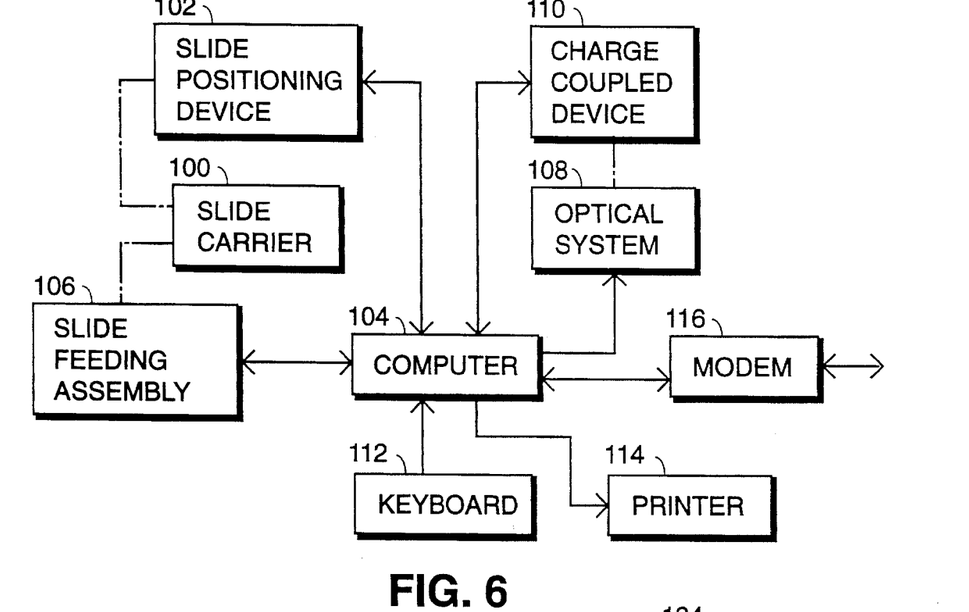
FIG. 6 is a block diagram of a computerized slide scanning system.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures. The texture and line scanning is repeated at different magnification levels.

Computer 104 may be connected to a keyboard 112, a printer 114, and a modem 116. Modem 116 forms part of a telecommunications link for connecting computer 104 to a remote data processing unit such as computer 64 in FIG. 4.

Image generating apparatus 42 in FIG. 1 may take the form of the computerized slide scanning system of FIG. 6.

Figure 7:
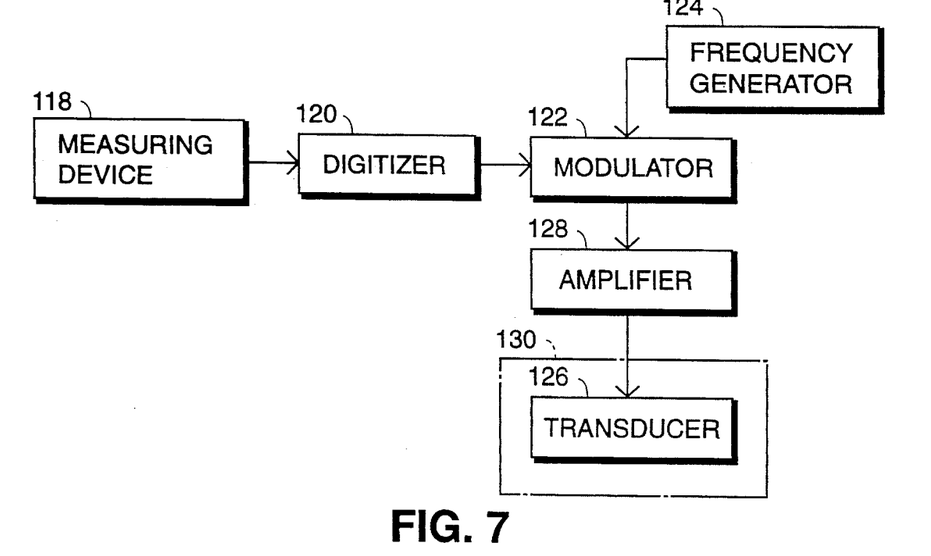
FIG. 7 is a block diagram of a device for measuring a diagnostic parameter and transmitting the measurement over the telephone lines.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a doppler study apparatus, an EEG machine, an EKG machine, an EMG machine, or a pressure measurement device, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electro-acoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in FIG. 4) which utilizes the incoming data to perform a diagnostic evaluation on the patient.

Monitoring and measuring device 118 may include traditional medical instrumentation such as a stethoscope or modern devices such as a CCD.

Figure 8:
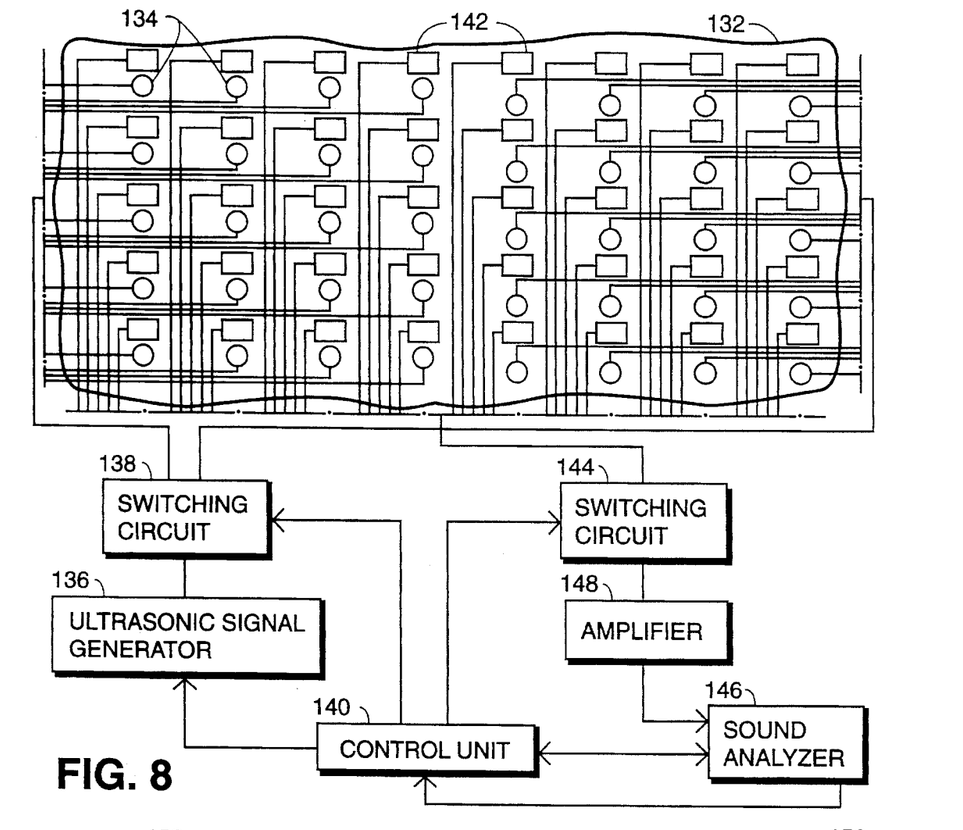
FIG. 8 is a diagram of an ultrasonography device.

FIG. 8 shows an ultrasonographic image generating apparatus which may be used in the medical diagnostic system of FIG. 1 (see reference designation 42) or in the medical diagnostic system of FIG. 4 (see reference designations 78a, 78b, . . . 78i). A flexible web 132 carries a plurality of piezoelectric electroacoustic transducers 134 in a substantially rectangular array. Tranducers 134 are each connectable to an ultrasonic signal generator 136 via a switching circuit 138. Switching circuit 138 is operated by a control unit 140 to connect tranducers 134 to signal generator 136 in a predetermined sequence, depending on the area of a patient's body which is being ultrasonically scanned.

Web 132 also carries a multiplicity of acousto-electric transducers or sensors 142 also arranged in a substantially rectangular array. Sensors 142 are connected to a switching circuit 144 also operated by control unit 140. An output of switching circuit 144 is connected to a sound analyzer 146 via an amplifier 148.

Web 132 is draped over or placed around a portion of a patient's body which is to be monitored ultrasonically. Control unit 140 then energizes signal generator 136 and operates switching circuit 138 to activate transducers 134 in a predetermined sequence. Depending on the transducer or combination of transducers 134 which are activated, control unit 140 operates switching circuit 144 to connect a predetermined sequence of sensors 142 to sound analyzer 146. Sound analyzer 146 and control unit 140 cofunction to determine three dimensional structural shapes from the echoes detected by sensors 142.

Control unit 140 is connected to ultrasonic signal generator 136 for varying the frequency of the generated signal.

Figure 9:
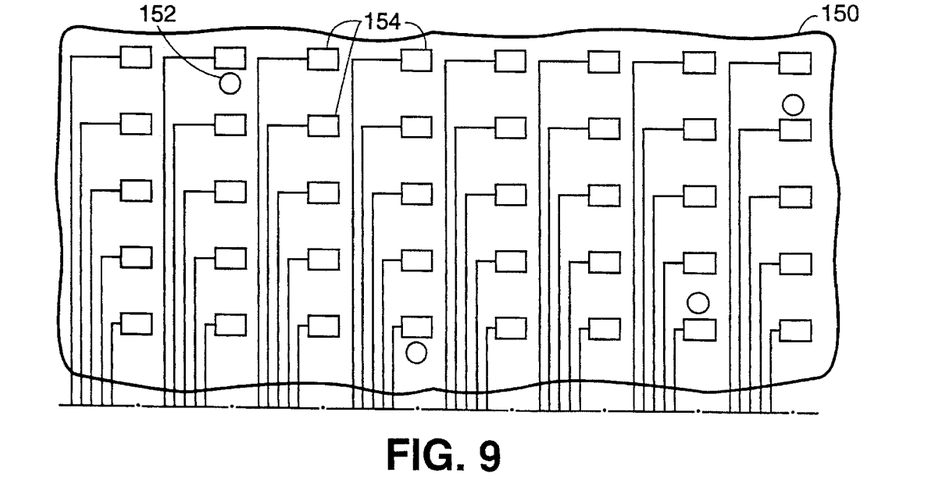
FIG. 9 is a diagram showing a modification of the device of FIG. 8.

FIG. 9 shows a modified ultrasonography web 150 having a limited number of electroacoustic transducers 152 and generally the same number and disposition of sensors 154 as in web 132.

Web 132 or 150 may be substantially smaller than illustrated and may corresponding carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined locations on the patient. Control unit 140 and sound analyzer 146 are programmed to detect internal organic structures from the data obtained at the different locations that the web 132 or 150 is juxtaposed to the patient.

Figure 10:
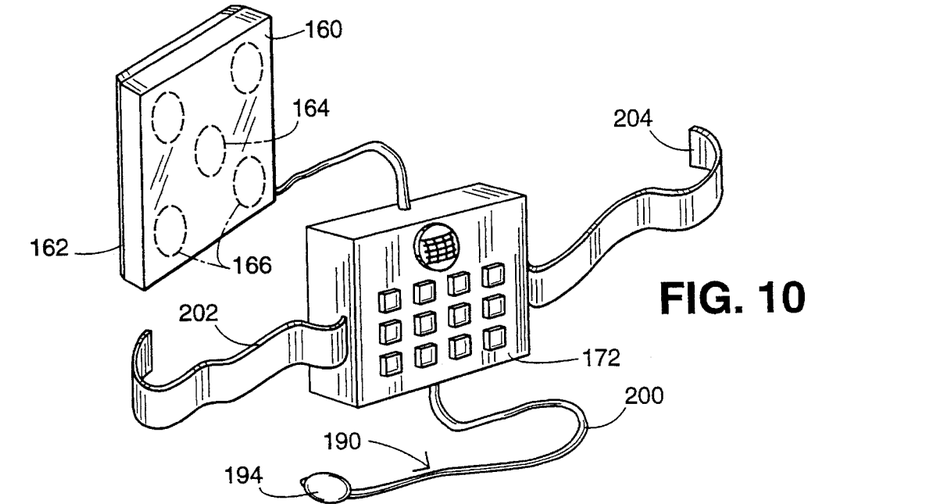
FIG. 10 is a schematic perspective view of a system for automatically diagnosing and treating internal structural changes signifying imminent dangerous conditions.
Figure 11:
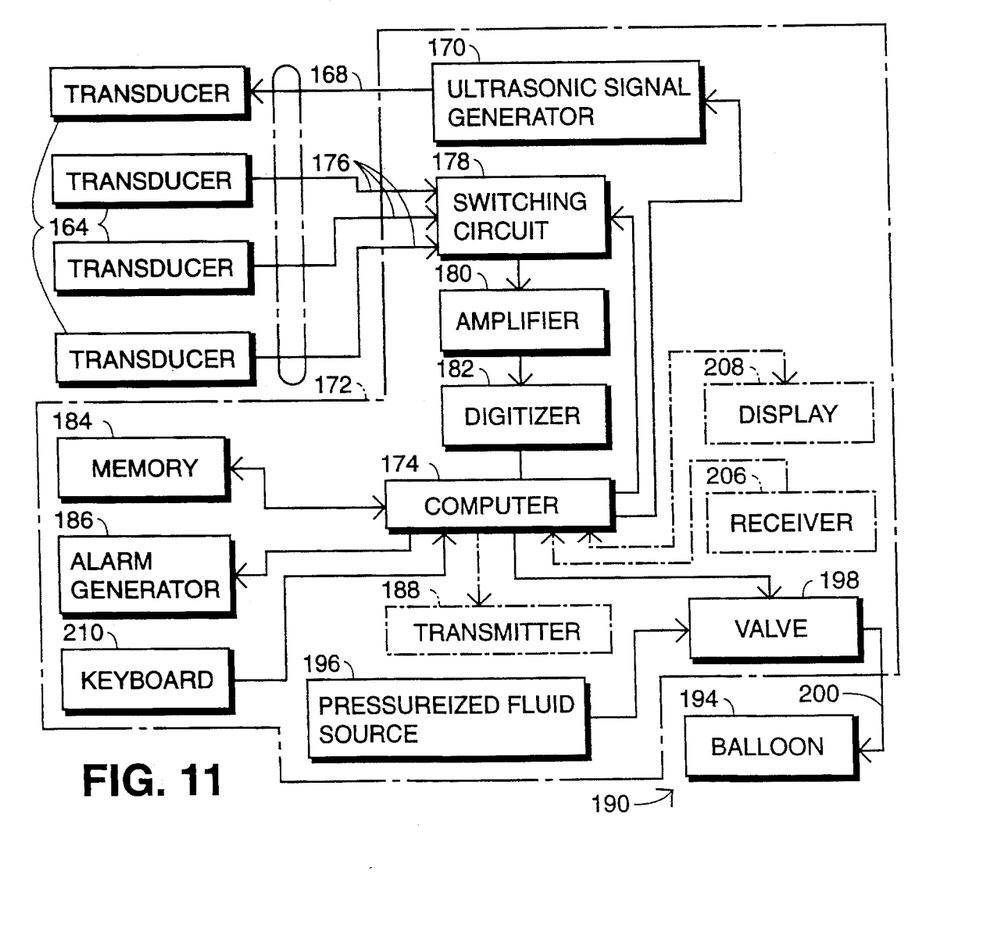
FIG. 11 is a block diagram of the system of FIG. 10.

As illustrated in FIGS. 10 and 11, a medical diagnostic and treatment system comprises a scanner pad 160 provided on one side with a two-sided (replaceable) adhesive layer 162 which is attachable to the skin of a patient in the region of the spleen or an aortic aneurysm for collecting individualized dimensional data about a splenic hematoma or the aneurysm. Pad 160 carries one or more ultrasonic electroacoustic transducers 164 and a plurality of ultrasonic acousto-electric transducers 166.

Transducer 164 is connected via a lead 168 to an ultrasonic signal generator 170 disposed in a housing 172 and energized periodically under the control of a microprocessor or computer 174, whereby transducer 164 produces ultrasonic pressure waves of a predetermined frequency and intensity for transmission through the organic tissues of the patient to the subject organ. The ultrasonic pressure waves are reflected by the organ, and particularly by the structural defect thereof, to transducers or sensors 166.

Transducers or sensors 166 are connected via respective leads 176 to a switching circuit 178 operated under the control of microprocessor 174. Ultrasonic-frequency electrical signals generated by transducers 166 are switched by circuit 178 to an amplifer 180 and a digitizer 182. Digitizer 182 is connected at an output to microprocessor 174.

The ultrasonic signals from transducers 166 are analyzed by microprocessor 174 to determined the shape, contours, dimensions, size, etc., of the subject organ or part of the organ. The results of this analysis are stored by microprocessor 174 in a memory 184.

Microprocessor 174 accesses memory 184 to compare previously stored dimensional data with incoming dimensional data to determine whether there has been any significant change in the size of the organ or organ part being monitored. In the event that microprocessor 174 detects such a change, an activating signal is fed by microprocessor 174 to an alarm generator 186. Alarm generator 186 may take the form of an electroacoustic transducer or loudspeaker or some other device which produces a cognizable signal recognized by hospital personnel. Alternatively or additionally, microprocessor 174 sends an electromagnetic activating signal via an optionally wireless transmitter 188 to a remote monitoring facility or station (not shown) in a hospital. An alarm may be generated at the remote station identifying the patient and the dangerous condition. Of course, the signal from microprocessor 174 is coded to identify the patient and the patient's location.

Switching circuit 178, amplifier 180, digitizer 182, microprocessor 174, memory 184, alarm generator 186 are all disposed in housing 172.

The system of FIGS. 10 and 11 further comprises a treatment device 190 operatively connected to microprocessor 174 and adapted for implantation into the patient for therapeutically affecting function of the subject organ to alleviate the possibly dangerous condition. Treatment device 190 specifically includes a balloon 194 inflatable with pressurized fluid from a source 196 upon opening of a valve 198 by microprocessor 174. Pressure source 196 and valve 198 are located in housing 172 and connected to balloon 194 via a catheter 200.

In the event that the organ being monitored is the spleen, balloon 194 and the distal end of catheter 200 are inserted into the femoral artery through the aorta and into the splenic artery. Balloon 194 is thereby positioned upstream of the spleen in the splenic artery. Upon detecting an increase in size of a splenic hematoma in response to the electrically encoded dimensional siganls from transducers 166, microprocessor 174 opens valve 198 and thereby inflates balloon 194 to block the splenic artery and prevent blood flow to the spleen. Hemorrhaging of the spleen from an imminent rupture of the hematoma is thus reduced or avoided.

Housing 172 is provided with a fastener such as a pair of straps 202 and 204 for attaching the housing to the waist of the patient. Alternatively, housing 172 may be provided with a clip (not shown) for secruing the housing to a belt worn by the patient.

In an alternative method for monitoring a patient, housing 172 carries a receiver 206 which may be a wireless receiver or may be connectable to a remote facility via a modem (not illustrated). Receiver 206 and transmitter 188 are periodically connected to the remote facility. Upon such a connection, the remote facility instructs microprocessor 174 to provide on a display 208 a message as to where pad 160 is to be placed on the user. Upon a placement of the pad, microprocessor 174 forwards dimension-encoding signals to the remote facility via transmitter 188. Further instructions are subsequently received by receiver 206 and displayed on display 208 under the control of microprocessor 174. Upon the collection of sufficient information, the remote facility may provide a final instruction to the user via display 208. Such a final instruction might be, for example, "Lie down and await ambulance," or "You are fine. Call again in an hour."

A keyboard 210 is provided on housing 172 for enabling the user to interact with microprocessor 174 to enable such a procedure. In addition, microprocessor 174 may be reprogrammed via keyboard 210 to periodically monitor the subject organ at intervals of different durations. Keyboard 210 is used to initialize and calibrate microprocessor 174.

Figure 12:
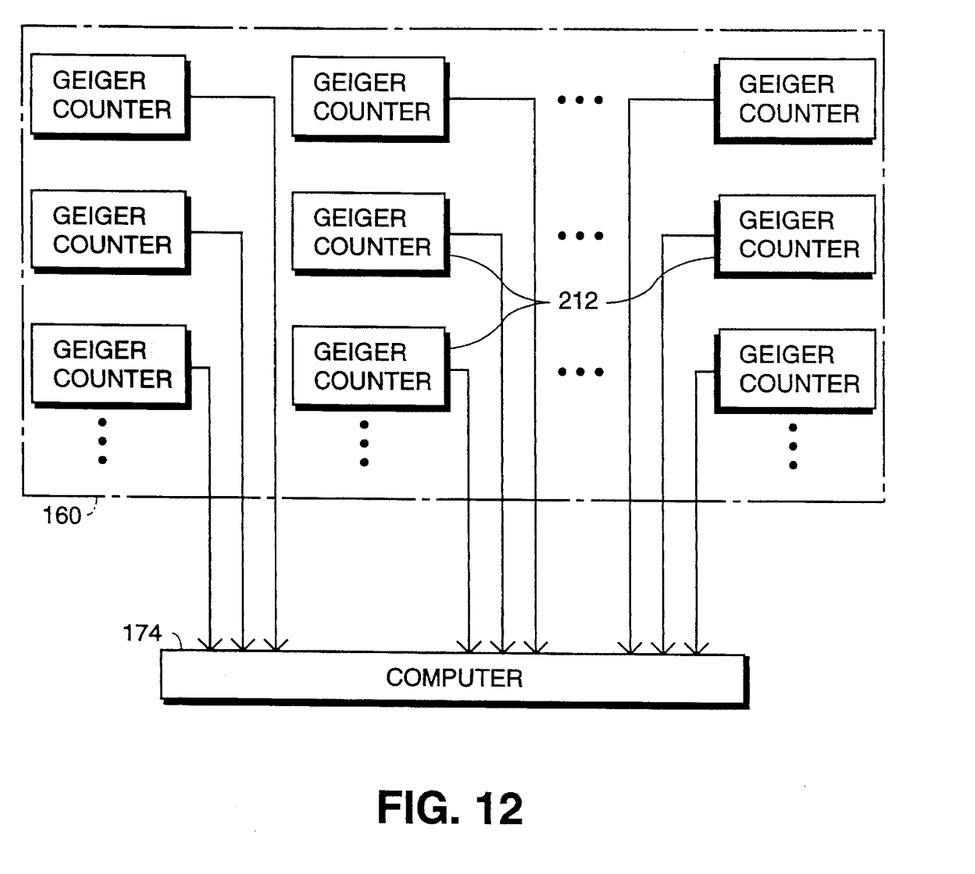
FIG. 12 is a block diagram of parts of a modification of the system of FIGS. 10 and 11.

FIG. 12 illustrates that the ultrasonic transducers 166 of the embodiment of FIGS. 10 and 11 may be replaced by a plurality of Geiger type counters 212 for monitoring the products of radiative decay. In this case, a radioactive substance is injected or otherwise dispensed within the body so as to be absorbed, for example, into the spleen. As the substance decays, the radioactive byproducts reveal the dimensions (shape, configuration, size) of the organ and its parts.

Figure 13:
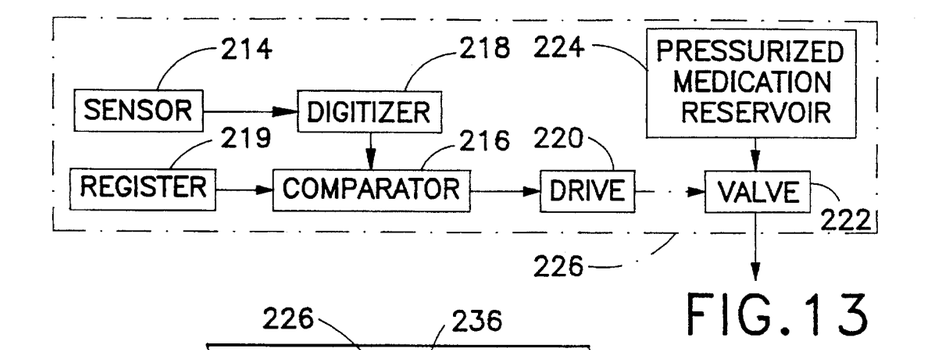
FIG. 13 is a block diagram of a medical treatment device in accordance with the present invention.

As depicted in FIG. 13, a medical treatment device comprises a sensor 214 functioning to at least periodically measure a predetermined physiological parameter of a patient. Sensor 214 generates an electrical signal encoding a measured value of the physiological parameter. A comparator 216 is operatively connected to sensor 214 via a digitizer 218 for comparing the measured value of the physiological parameter with a predetermined threshold value for the physiological parameter, stored in a register or memory element 219, to determine whether the measured value of the physiological parameter has passed the threshold value. In the event that comparator 216 determines that the predetermined threshold value has been passed, the comparator transmits a signal to a drive element 220 such as a solenoid or miniature electric motor to open a valve 222 and thereby permit a preselected medication or chemical composition to become injected into the patient from a pressurized reservoir 224. The medication or chemical composition is selected to treat a prediagnosed illness of the patient, the illness being characterized by a detectable change in the measured physiological parameter. At least some of the components 214, 216, 218, 220, 222, and 224 of the medical treatment device of FIG. 13 are contained in a common casing or housing 226 which is attachable to the patient as described in detail hereinafter.

Figure 14:
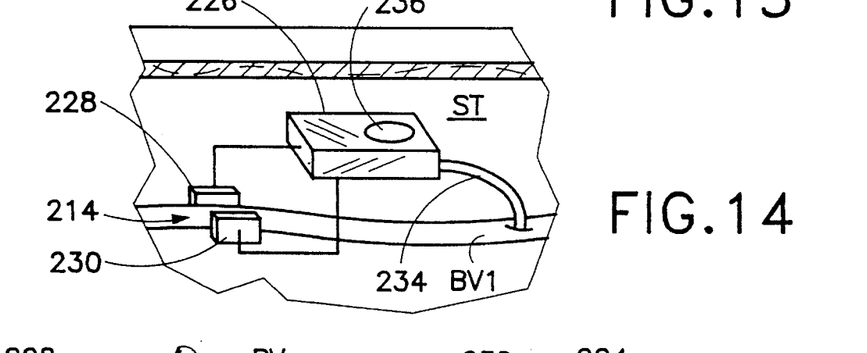
FIG. 14 is a schematic perspective view showing a particular embodiment of the medical treatment device of FIG. 13 implanted subcutaneously.
Figure 15:
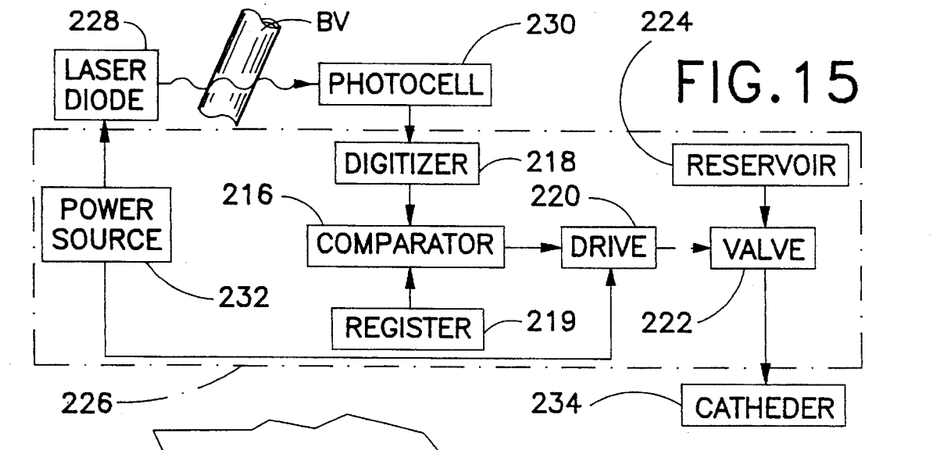
FIG. 15 is a block diagram showing functional components of the device of FIG. 14, with repeated reference numerals designating components also illustrated in FIG. 13.

FIGS. 14 and 15 illustrate a specific embodiment of the device of FIG. 13 wherein the device is particularly adaptd for monitoring the level of a blood constituent such as glucose molecules or calcium ions. Sensor 214 takes the form of a laser diode 228 and a photocell 230 acting in cooperation with one another to monitor concentration or level of the selected blood constituent. Laser diode 228 and photocell 230 are implanted into the patient on opposite sides of a selected blood vessel BV1. Laser diode 228 is energied by a power supply 232 housd in casing 226. Casing 226 is also implanted into the patient, for example, in subcutaneous tissues ST.

The medical treatment device of FIG. 14 is attached to the vascular system of the patient by a catheter 234 which extends from casing 226 to blood vessel BV1. Where glucose levels are being monitored, comparator 216 operates drive element 220 to open valve 222 and thereby inject insulin into the patient's vascular system from reservoir 224 via catheter 234, upon detecting that the level of glucose molecules in the patient's blood is greater than a predetermined limit, stored in encoded form in register 219. Where calcium ion level is being monitored, comparator 216 induces the injection into the blood stream of a known substance for reducing the level of calcium ions, upon detecting that the calcium ion level has dropped below a pre-established threshold (a Characteristic symptom of hyperparathyroidism).

It is to be noted that sensor 214, particularly laser diode 228, is tuned, upon implantaton of the medical device into the patient and upon the subsequent attainment of temperature equilibrium inside the patient, to emit electromagnetic radiation of a characteristic frequency absorbed by the target blood constitutent, whether glucose molecules, calcium ions or some other substance. The blood concentration of the target substance is proportional to a decrease in the amount of the characteristic electromagnetic frequency transmitted through the blood vessel. It is to be further noted that casing 226 maybe provided with a self-sealing membrane 236 permitting access to reservoir 224 for refilling the reservoir with insulin or another preselected treatment agent via a hypodermic syringe (not illustrated).

Figure 16:
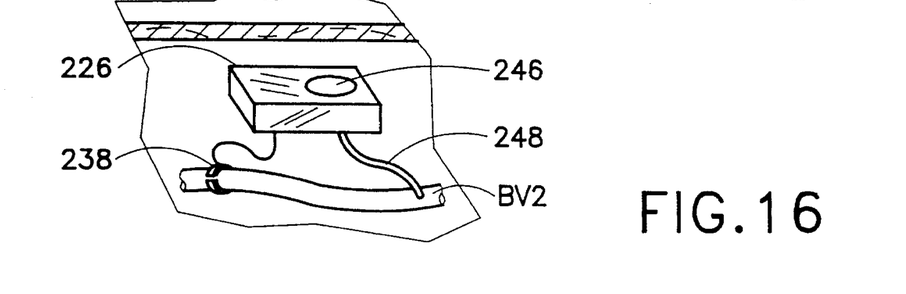
FIG. 16 is a schematic perspective view showing another particular embodiment of the medical treatment device of FIG. 13 implanted into a patient's body.
Figure 17:
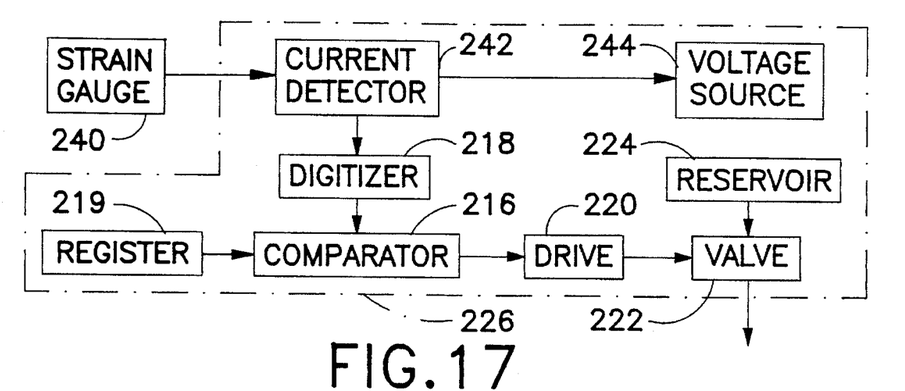
FIG. 17 is a block diagram showing functional components of the device of FIG. 16, with repeated reference numerals designating components also illustrated in FIG. 13.

FIGS. 16 and 17 show a particular embodiment of the medical treatment device of FIG. 13 which is adapted for treating low blood pressure. Sensor 214 (FIG. 13) takes the form of a partially flexible slotted cuff 238 (FIG. 16) inserted about a blood vessel BV2 and including a sensitive strain gauge 240 (FIG. 17) for measuring changes in size of the blood vessel owing to variations in blood pressure. The monitoring of changes in blood pressure is implemented in part by a current detector 242 operatively connected to strain gauge 238 for measuring minute changes in the electrical resistance of the strain gauge. A voltage source 244 supplies the power for the electrical current carried by strain gauge 240. Current detector 242 and voltage source 244 are disposed inside casing 226, along with comparator 216, digitizer 218, register 219, drive 220, valve 222 and reservoir 224. Again, housing or casing 226 may be provided with a self-sealing membrane 246 for enabling a periodic replenishment of a chemical treatment agent or medication in reservoir 224.

Upon detecting that the pressure in blood vessel BV2 has fallen below a pre-established threshold value, contained in encoded form in register or memory 219, comparator 216 issues a signal controlling drive 220 to open communication between reservoir 224 and a catheter 248 which attaches casing 226 and particularly reservoir 224 to blood vessel BV2. This action serves to treat the patient with a prescribed aliquot of a known chemical therapeutic agent for increasing blood pressure.

Figure 18:
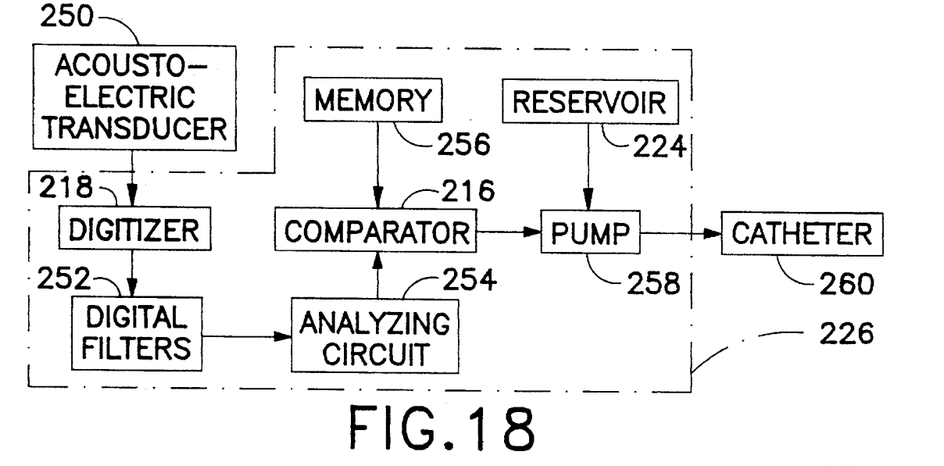
FIG. 18 is a block diagram showing functional components of a further particular embodiment of the device of FIG. 13, with repeated reference numerals designating components also illustrated in FIG. 13.

FIG. 18 depicts a specific modificaton or realization of the medical treatment device of FIG. 13 which is adapted for treating various irregularities (arrythmias) in heart action. Sensor 214 (FIG. 13) is thus adaptd to monitor an electrocardiographic rhythm and includes an acousto-electric transducer 250 (FIG. 18) implanted into the patient at a location suitable for detecting pressure waves in the patient arising from the patient's heart action. Transducer 250 is connected via digitizer 218 to a digital filter or filters 252 which serve to remove irrelevant pressure waves (noise) arising from sources other than heart action. The function of filters 252 is perfored also, to a finer degree, by a preprogramed analyzing circuit 254 which is operatively connected to acousto-electric transducer 250 for discriminating between acoustic input due to heart action and acoustic pressure waves arising from other sources. Comparator 216 is operatively connected to analyzing circuit 254 for comparing an electrocardiographic rhythm, as determined through transducer 250 and analyzing circuit 254, with a plurality of thresholds characterizing normal and abnormal cardiac rhythms. These thresholds are stored in encoded form in a relatively expanded register or memory 256.

Upon detecting an arrythmia prediagnosed as indicative of a dangerous condition, comparator 216 energizes a pump 258 which delivers a known chemical treatment agent from reservoir 224 to a catheter 260 extending to a blood vessel (not ilustrated) of the patient.

It is to be noted that pump 258 performs the medication delivery or treatment functions of drive 220 and valve 22 of FIG. 13. Pump 258 may replace drive 220 and valve 222 in the embodiments of FIGS. 14–17. It is to be noted further that other equivalent techniques for monitoring heart action may be used in implementing the objects of the device of FIG. 18. For example, heart action may be monitored by electrodes (not shown) disposed at preselected locatons inside the patient which are sensitive to electrical potentials arising from heart activity, for example, on the heart wall itself or even on other organs such as ribs.

Figure 19:
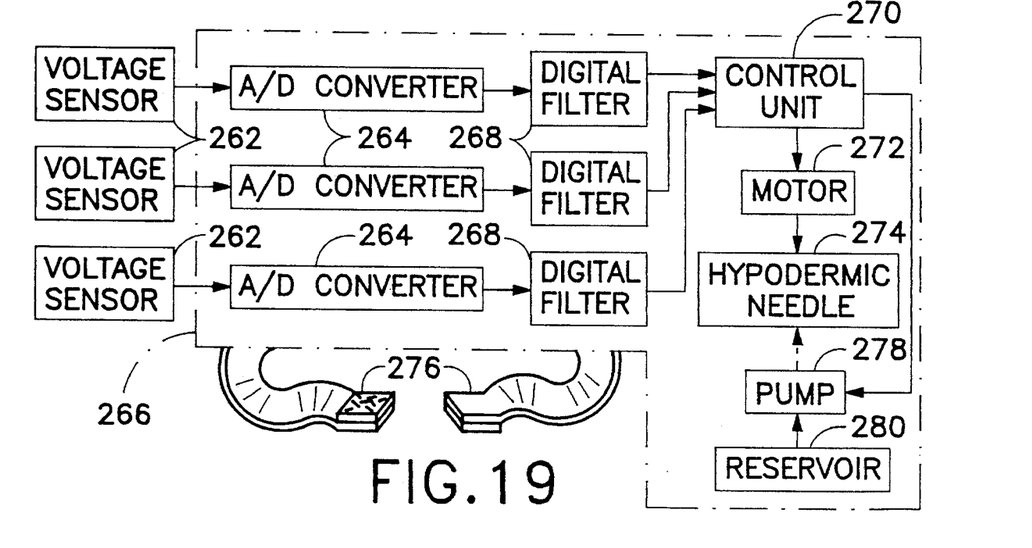
FIG. 19 is a block diagram showing functional components of yet another particular embodiment of the device of FIG. 13, with partially repeated reference numerals.

In all of the particular embodiments of the automatic medical treatment device of FIG. 13 illustrated in FIGS. 14–18, it is generally contemplated that the medical treatment device is implanted into the patient. FIG. 19 shows a specific embodiment of the device which is intended to remain outside of the patient. A plurality of voltage sensors or electrodes 262 are positionable on an external skin surface of the patient (e.g., the patient's chest) and are connected to respective digitizers of analog-to-digital (A/D) converters 264 disposed inside a casing 266. Converters 264 feed respective digital filters 268 and the filtered outputs are transmitted to a control unit 270. Control unit 270 may take the form of a microprocessor programmed to analyze incoming signals to parameterize heart activity. Control unit 270 compares the parameterized signals with internally stored ranges or limits for those parameters. When the derived parameters fall outside the normal ranges, control unit 270 energizes a motor 272 to insert a hypodermic needle 274 from casing 266 through the patient's skin and into an underlying vein. To that end, straps 276 serve to attach casing 266 about the patient's wrist, waist or some other limb over a vein.

Also upon determining from measured or derived parameters that the patient's heart is experiencing prediagnosed abnormal activity, control unit 270 energizes a pump 278 to convey fluidic medication from an internal reservoir 280 to the patient's vascular system via the inserted hypodermic needle 274.

It is to be understood that other physiological parameters such as blood pressure may be monitored externally and treated via injection trough an automatically inserted hypodermic needle, as described above with reference to FIG. 19. It is to be further understood that other equivalent delivey techniques may be employed in addition to or as alternatives to the technique of FIG. 19. For example, medication may be injected via high pressure directly through the skin surface. This alternative technique is useful, for example, where the patient is suffering from heightened sensitivity to insect bites.

It is to be further understood that sensor 214 (FIG. 13) may be separate from casing 226 and connected to comparator 216 and treatment componentry via a receiver/transmitter combination (not illustrated).

In using the device of FIG. 13, the predetermined physiological parameter is measured at least periodically. A signal is generated encoding a measured value of the physiological parameter, that essentially real time or instantaneous measured value being automatically compared with a predetermined threshold value to determine whether the measured value exceeded the threshold value. In the event that the measured value has been exceeded, a predetermined chemical composition is automatically injected into the patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A medical device comprising:

sensor means for at least periodically measuring a predetermined physiological parameter of a patient and for generating a signal encoding a measured value of said physiological parameter;

comparator means operatively connected to said sensor means for comparing the measured value of said physiological parameter with a predetermined threshold value for said physiological parameter to determine whether the measured value of said physiological parameter has passed said threshold value;

treatment means operatively connected to said comparator means for automatically injecting a predetermined chemical composition into the patient upon a determination by said comparator means that the measured value of said physiological parameter has passed said threshold value, said treatment means including a hypodermic needle and means operatively connected to said hypodermic needle for automatically inserting said hypodermic needle subcutaneously; and attachment means for attaching said sensor means, said comparator means and said treatment means to the patient.

2. The device defined in claim 1 wherein said sensor means includes means for detecting a concentration of a blood constituent.

3. The device defined in claim 2 wherein said sensor means includes means implanted into the patient and juxtaposed to a blood vessel of the patient for detecting a glucose level in the blood and wherein said predetermined chemical composition is insulin.

4. The device defined in claim 3 wherein said means for detecting includes a laser diode and a photocell.

5. The device defined in claim 4 wherein said sensor means, said comparator means and said treatment means are implanted subcutaneously, said attachment means including a catheter extending from said treatment means to a vein or artery.

6. The device defined in claim 5 wherein said vein or artery is the same as said blood vessel.

7. The device defined in claim 1 wherein said attachment means includes a catheter inserted into a blood vessel of the patient, said catheter extending from said treatment means.

8. The device defined in claim 1 wherein said physiological parameter is blood pressure, said sensor means including monitoring means for detecting blood pressure of the patient, said comparator means including means for comparing, with a pre-established blood pressure threshold, blood pressure measurements made by said monitoring means.

9. The device defined in claim 8 wherein said sensor means, said comparator means and said treatment means are implanted into the patient, at a position proximate to a blood vessel.

10. The device defined in claim 1 wherein said physiological parameter is an electrocardiographic rhythm, said sensor means including acousto-electric transducer means for detecting heart action, further comprising analyzing means operatively connected to said acousto-electric transducer means for discriminating between acoustic input due to heart action and acoustic pressure waves arising from other sources, said comparator means being operatively connected to said analyzing means for comparing an electrocardiographic rhythm, as determined through said sensor means and said analyzing means, with a plurality of thresholds characterizing normal and abnormal cardiac rhythms.

11. A medical device comprising:

sensor means for at least periodically measuring a predetermined physiological parameter of a patient and for generating a signal encoding a measured value of said physiological parameter;

comparator means operatively connected to said sensor means for comparing the measured value of said physiological parameter with a predetermined threshold value for said physiological parameter to determine whether the measured value of said physiological parameter has passed said threshold value;

treatment means operatively connected to said comparator means for automatically injecting a predetermined chemical composition into the patient upon a determination by said comparator means that the measured value of said physiological parameter has passed said threshold value;

a casing disposed outside the patient, said sensor means, said comparator means and said treament means being mounted to said casing; and attachment means including a wristband connected to said casing for attaching said sensor means, said comparator means and said treatment means to the patient.

12. A medical method comprising the steps of:

implanting a photodiode and a photocell into a patient on opposite sides of a blood vessel;

at least periodically measuring a concentration of a blood constitutent of the patient, said step of measuring including the step of operating said photodiode to emit light of a characteristic frequency into the blood vessel, said step of measuring further including the step of operating said photocell to detect a concentration of said blood constitutent in the blood of the patient;

generating a signal encoding a measured value of said concentration;

automatically comparing the measured value of said concentration with a predetermined threshold value for said concentration to determine whether the measured value of said concentration has passed said threshold value; and automatically subcutaneously injecting a predetermined chemical composition into the patient upon determining that the measured value of said concentration has passed said threshold value.

13. The method defined in claim 12 wherein said blood constituent is glucose and said chemical composition is insulin.

14. The method defined in claim 12 wherein said step of injecting includes the step of injecting said chemical composition into a blood vessel of the patient through a catheter extending to said blood vessel.

15. The method defined in claim 12 wherein said step of injecting includes the step of injecting said chemical composition into a vein or artery of the patient.

16. The method defined in claim 15 wherein said step of injecting includes the step of automatically inserting a hypodermic needle subcutaneously.

* * * * *